United States Patent [19]
Rinehart et al.

[11] Patent Number: 6,034,058
[45] Date of Patent: Mar. 7, 2000

[54] SEMI-SYNTHETIC ALANYL DILEMNIN ANALOGS

[76] Inventors: Kenneth L. Rinehart, 1306 S. Carle Ave., Urabana, Ill. 61801; Alexandra J. Sanborn, 1003A Smith Rd., Urbana, Ill. 61802; George R. Wilson, # 204, 906 Harding Dr., Urbana, Ill. 61801

[21] Appl. No.: 09/058,508

[22] Filed: Apr. 10, 1998

Related U.S. Application Data

[60] Provisional application No. 60/043,329, Apr. 15, 1997.
[51] Int. Cl.[7] .............................. A61K 38/12; C07K 7/54
[52] U.S. Cl. ............................ 514/11; 530/317; 530/323; 530/330; 530/331
[58] Field of Search .............................. 514/11; 530/317, 530/323, 329, 330, 331, 857

[56] References Cited

U.S. PATENT DOCUMENTS

| | | | |
|---|---|---|---|
| 4,493,796 | 1/1985 | Rinehart, Jr. ............................ | 530/317 |
| 4,948,791 | 8/1990 | Rinehart, Jr. et al. .................. | 514/183 |
| 5,137,870 | 8/1992 | Rinehart ................................. | 514/10 |
| 5,294,603 | 3/1994 | Rinehart ................................. | 514/10 |
| 5,834,586 | 11/1998 | Rinehart et al. ....................... | 530/322 |

OTHER PUBLICATIONS

Mayer et al, Synthesis of New Didemnin B Analogs., vol. 59, No. 18, pp. 5192–5205, 1994.

*Primary Examiner*—Jeffrey E. Russel
*Attorney, Agent, or Firm*—Ernest V. Linek; Banner & Witcoff, Ltd

[57] ABSTRACT

The didemnin class of biologically active cyclodepsipeptides, isolated from the marine tunicate *Trididemnun solidum*, has shown considerable antitumor, antiviral, and immunosuppressive activities. Didemnin B (DB) and most other natural didemnins contain a common macrocycle and differ only in the composition of the side chain. In the present invention, structural modifications were introduced in the side chain to afford several didemnin analogues for structure-activity relationship studies. The latter have shown that the linear side chain portion of the didemnin core structure can be altered and, in some cases, provide significant gains in bioactivities. Of the compounds synthesized the new [Ala$^9$] didemnin B is the most active against the L1210 (murine leukemia) cell line, at the 0.04 ng/mL level.

21 Claims, No Drawings

SEMI-SYNTHETIC ALANYL DILEMNIN ANALOGS

CROSS-REFERENCE TO RELATED APPLICATION

This application claims the benefit of U.S. Provisional Application Ser. No. 60/043,329 filed Apr. 15, 1997, the teachings of which are incorporated herein by reference.

BACKGROUND OF THE INVENTION

Didemnin compounds were first reported by Rinehart et al. as isolates from the Caribbean tunicate *Trididemnum solidum* in 1981. These cyclic depsipeptides possess a variety of biological activities including in vitro and in vivo antiviral, antitumor, and immunosuppressive activities. They are potent inhibitors of L1210 leukemia cells in vitro, and are also active in vivo against P388 leukemia and B16 melanoma. Didemnin B, a particularly active compound of this class, is approximately twenty times more cytotoxic than didemnin A in vitro and has undergone phase II clinical trials for antitumor activity. Both didemnins A and B exhibit antiviral activity against DNA and RNA viruses, with didemnin B being more active. The structures of didemnins A and B have been established as 1 and 2, respectively.

Although many studies have shed light on the pharmacology and chemistry of didemnins, little is known about their mechanism of action. However, recent biochemical studies of possible binding sites have provided promising results. Studies performed by Shen et al. have shown that didemnin B binds to a site on Nb2 node lymphoma cells and that this binding may be responsible for the immunosuppressive activity. Crews et al. have reported that didemnin A binds elongation factor-1α (EF-1α) in a GEP-dependent manner which suggests EF-1α may be the target responsible for the ability of didemnins to inhibit protein synthesis.

SUMMARY OF THE INVENTION

The present invention is directed to semi-synthetic didemnin analogues in which structural modifications were introduced in the side chain for investigating structure-activity relationships. The syntheses of several didemnin derivatives including the new analogues[Ala$^9$]-didemnin B (3), Gln-[Ala$^9$]-didemnin B (4), [Ala$^9$]-Didemnin M (5), Pro-Didemnin A (6), and Ala-Didemnin A (7) have been performed. [Ala$^9$]-didemnin B, the most active of the didemnins synthesized thus far, contains alaninyl in place of the latyl unit. Preliminary assay results reveal that alterations of the linear side-chain portion via alaninyl units may enhance bioactivities.

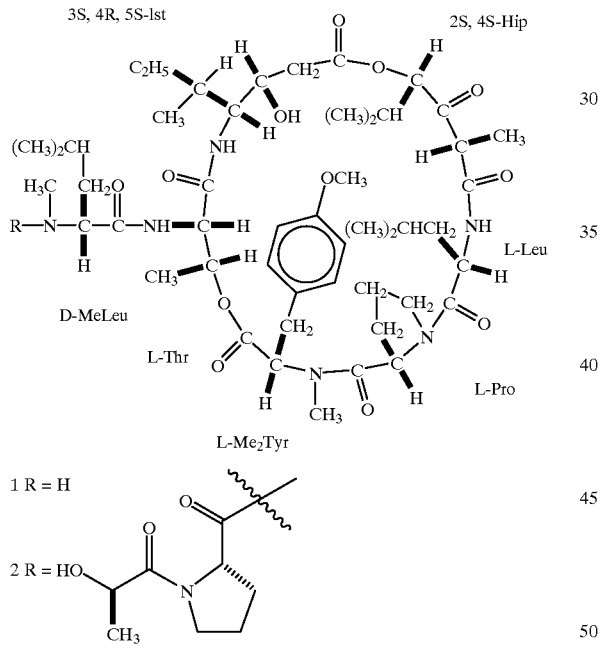

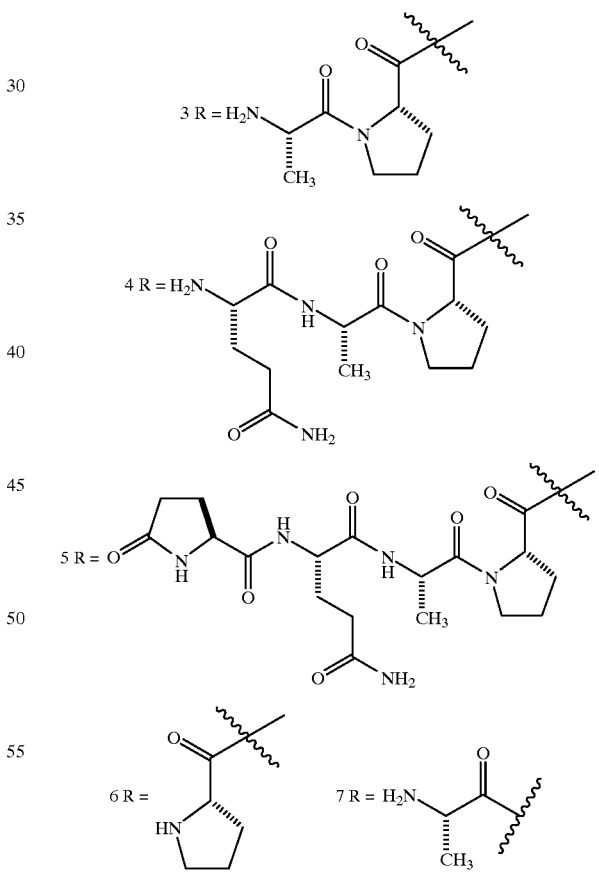

The structures of Didemnins A and B

Structure-activity relationship studies have been somewhat limited due to the restricted number of available modifications of the extracted natural compounds. Although the bioactivity of didemnin B has been attributed to its α-(α'-hydroxyisovaleryl)propionyl (Hip) group and its side chain, few other structural features have been examined. An X-ray crystal structure of didemnin B by Hossain, et al. shows that the β-turn side chain, the isostatine hydroxyl group, and the tyrosine residue extend outward from the rest of the molecule, leading to speculation about their importance for biological activity. Structural changes in those areas have shown some of these features to be useful for activity.

The side chain structures of synthetic didemnin analogues

The exceptional biological activities of the didemnins, combined with the necessity for a more reliable source of these cyclic depsipeptides, make their syntheses of particular interest. Didemnin A is the most abundant of these compounds, therefore, it serves as the starting point for the syntheses of these other didemnin analogues. The alaninyl derivative of didemnin B will serve as the preliminary synthetic target as it can be synthesized from the natural source of didemnin A. After obtaining sufficient quantities of [Ala$^9$]-didemnin B, the synthetic routes towards the glutaminyl didemnin analogues can be performed. Synthetic studies towards the preparation of these didemnin analogues will be of high significance for in vivo testing and the development of these compounds as potential drugs and/or pharmacological tools.

DETAILED DESCRIPTION OF THE INVENTION

The retrosynthetic disconnections, which formed the basis of a plan for synthesizing the alaninyl analogue of didemnin B (3), are outlined below. Disconnection of the amide function between didemnin A and the side chain unit gave two components, didemnin A (1) and the dipeptide (8).

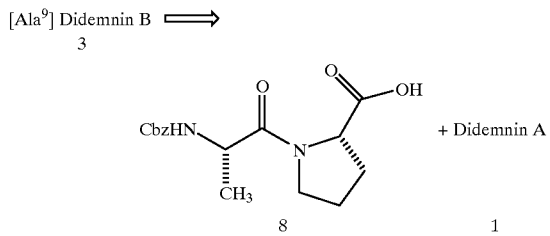

Retrosynthetic analysis of [Ala$^9$] Didemnin B

The synthesis of dipeptide 8 was accomplished by coupling of Cbz-Alanine (9) with ProOMe (10) followed by saponification to provide 8. Coupling of the protected dipeptide unit with didemnin A afforded the protected derivative 9. Hydrogenation affords the alaninyl derivative (3) which upon HPLC purification using a gradient system of $CH_3CN/H_2O$ shows a single peak.

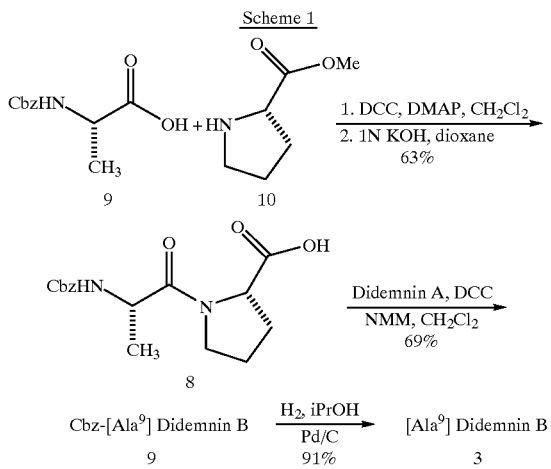

Various other analogues were synthesized using a series of protection, coupling, and deprotection. Namely, the glutaminyl derivative (4) pyroglutamyl derivative, and the didemnin M analogue (5). As outlined in scheme II, [Ala$^9$] didemnin B (3) was coupled with the protective form of glutamine (10) to provide 11 after HPLC purification. Deprotection via hydrogenation afforded the glutaminyl analogue 4. A sufficient amount of 4 was prepared and then coupled with the protected form of pyroglutamic acid to provide the protected alaninyl derivative of didemnin M (12). Upon purification via reversed phase HPLC, the compound was then treated to under an atmosphere of hydrogen to afford [Ala$^9$] didemnin M (5).

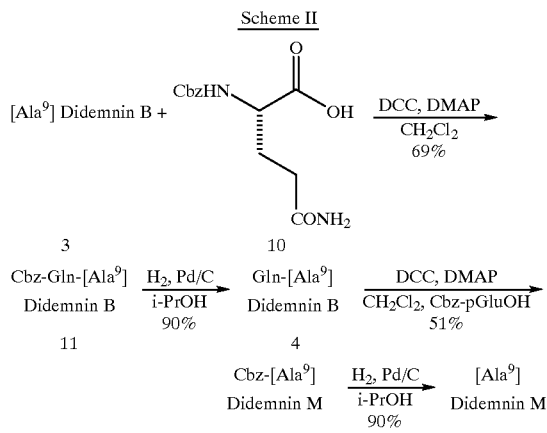

The remaining analogues were synthesized by coupling didemnin A to the appropriate amino acid unit. Thus, prolyl and alaninyl didemnin A were synthesized by coupling Cbz-proline of Cbz-alanine with didemnin A to provide the protected analogues. Removal of the protecting group afforded analogues 6 and 7. Glutaminyl analogues of alaninyl didemnin A were synthesized using the same series of protection, coupling, and deprotection as outlined above in Scheme II.

A summary of their bioactivities is shown below in Table 1.

TABLE 1

Cytotoxicities of Some Didemnins

| Compound | L1210, IC$_{90}$ (ng/mL) | Compound | L1210, IC$_{90}$ (ng/mL) |
|---|---|---|---|
| [Ala$^9$]DB | 0.04 | Prolyl DA | 12 |
| Cbz-[Ala$^9$]DB | 2 | [Ala$^9$]DB | 20 |
|  |  | Glutaminyl-AlaDA | 25 |
|  |  | Cbz-pGlu-Gln-[Ala$^9$]DB | 40 |
|  |  | Didemnin A | 75 |
| Cbz-Alaninyl DA | 3 | Cbz-pGlu-Gln-[Ala$^9$]DB | 200 |
|  |  | Cbz-pGlu-[Ala$^9$]DB | 200 |
| Didemnin B | 7 | Gln-[Ala$^9$]DB | 200 |
| Cbz-Glutaminyl DA | 8 | Cbz-[Ala$^9$]DM | 400 |
| Alaninyl DA | 8 | pGlu-[Ala$^9$]DB | 500 |

As shown above, the present invention is directed to bioactive compounds. These compounds have been prepared in substantially pure form, i.e., at a purity level sufficient to allow physical and biological characterization thereof. As described above, these compounds have been found to possess specific antitumor activities and as such they will be useful as medicinal agents in mammals, particularly in humans. Thus, another aspect of the present invention concerns pharmaceutical compositions containing the active compounds identified herein and methods of treatment employing such pharmaceutical compositions.

The active compounds of the present invention exhibit antitumor activity. Thus, the present invention also provides a method of treating any mammal affected by a malignant tumor sensitive to these compounds, which comprises administering to the affected individual a therapeutically effective amount of an active compound or mixture of compounds, or pharmaceutical compositions thereof. The present invention also relates to pharmaceutical preparations, which contain as active ingredient one or more of the compounds of this invention, as well as the processes for its preparation.

Examples of pharmaceutical compositions include any solid (tablets, pills, capsules, granules, etc.) or liquid (solutions, suspensions or emulsions) with suitable composition or oral, topical or parenteral administration, and they may contain the pure compound or in combination with any carrier or other pharmacologically active compounds. These compositions may need to be sterile when administered parenterally.

The correct dosage of a pharmaceutical composition comprising the compounds of this invention will vary according to the particular formulation, the mode of application, and the particular situs, host and bacteria or tumor being treated. Other factors like age, body weight, sex, diet, time of administration, rate of excretion, condition of the host, drug combinations, reaction sensitivities and severity of the disease shall be taken into account. Administration can be carried out continuously or periodically within the maximum tolerated dose.

The present invention will be further illustrated with reference to the following examples which aid in the understanding of the present invention, but which are not to be construed as limitations thereof. All percentages reported herein, unless otherwise specified, are percent by weight. All temperatures are expressed in degrees Celsius.

General Procedures.

$^1$H NMR spectra were recorded on Varian XL-200, General Electric QE-300, Varian XL-400, and General Electric QN-500 spectrometers. $^1$H Chemical shifts are referenced in $CDCl_3$ and $CD_3OD$ to residual $CHCl_3$ (7.26 ppm) and $CD_2HOD$ (3.34 ppm). Electron impact (EI) mass spectra were recorded on a Finnigan MAT CH-5 DF spectrometer. High resolution (HRFAB) and fast atom bombardment (FAB) mass spectra were recorded on a VG ZAB-SE mass spectrometer operating in the FAB mode using magic bullet matrix. Microanalyses were obtained by the School of Chemical Sciences Microanalytical Laboratory. Infrared (IR) spectra were obtained on an IR/32 FTIR spectrophotometer. Solid samples were analyzed as $CHCl_3$ solutions in NaCl cells. Liquids or oils were analyzed as neat films between NaCl plates.

Optical rotations (in degrees) were measured with a DIP 360 or a DIP 370 digital polarimeter with an Na lamp (589 nm) using a 5-x0.35-cm (1.0 mL) cell. Melting points were determined on a capillary melting point apparatus and are not corrected. Normal phase column chromatography was performed using Merck-kieselgel silica gel (70–230 mesh). Fuji-Davison C18 gel (100–200 mesh) was used for reversed phase column chromatography. All solvents were spectral grade. Analytical thin layer chromatography was performed on precoated plates (Merck, F-254 indicator). These plates were developed by various methods including exposure to ninhydrin, iodine, or UV light (254 nm). HPLC was performed with a Waters 990 instrument and an Econosil $C_{18}$ column (Alltech/Applied Science) or a Phenomenex $C_{18}$ column.

THF was distilled from sodium benzophenone ketyl and $CH_2Cl_2$ from $P_2O_5$. Dimethylformamide (DMF), triethylamine ($Et_3N$), and N-methylmorpholine (NMM) were distilled from calcium hydride and stored over KOH pellets. Pyridine was distilled from KOH and stored over molecular sieves. Other solvents, used without purification in reactions, were reagent grade without purification. Di-tert-butyl dicarbonate [$(Boc)_2O$], dicyclohexylcarbodiimide (DCC), dimethylaminopyridine (DMA), 1-hydroxybenzotriazole (HOBT), L-glutamine, L-pyroglutamic acid, L-alanine, and L-proline were obtained from the Aldrich Chemical Company. All reactions requiring anhydrous conditions were performed under an atmosphere of nitrogen.

EXAMPLE 1

N-Benzyloxycarbonyl-L-Alaninyl-L-proline methyl ester (Cbz-L-Ala-L-Pro-OMe)

L-Proline methyl ester (2.13 g, 12.9 mmol) in $CH_2Cl_2$, DMAP (71.2 mg) and DCC (3.57 g, 17.8 mmol) were added at 0° C. to a solution of 9 (2.79 g, 12.5 mmol). The solution was allowed to warm to room temperature and stirred for 12 h. Dicyclohexylurea was filtered and washed with ethyl acetate. The filtrate and washings were combined and washed with 10% citric acid, 5% sodium bicarbonate and water, dried over $MgSO_4$ and concentrated. The crude residue was purified by flash chromatography, eluting with hexane and ethyl acetate (4:1) to obtain the product, (2.98 g, 69%) as an orange oil; $^1$HNMR (500 MHz, $CDCl_3$) δ7.36–7.41 (5 H,m), 5.10 (2 H,s), 5.60 (1 H,d), 4.58 (1 H,m), 3.75 (2 H,m), 3.70 (3 H,s), 3.60 (1 H, m), 2.30–2.00 (4 H, m), 1.40 (3 H, d); FABMS 373.1 (M+K), 335.1 (M+H); HRFABMS Calcd for $C_{17}H_{23}N_2O_5$ (M+H) 335.1607, Found 335.1606.

EXAMPLE 2

N-Benzyloxycarbonyl-L-Alaninyl-L-proline (Cbz-L-Ala-L-ProOH, 8)

Cbz-L-Ala-L-ProOMe (0.58 g, 2.60 mmol) was dissolved in dioxane (4.05 mL) and 1N KOH (2.02 mL) was slowly added to the mixture at 0° C. The solution was stirred for 2 h. TLC analysis (EtOAc/hexane 1/1) showed the reaction to be complete. The mixture was neutralized using 2N HCl. The solvent was then evaporated. The solution was partitioned between ethyl acetate and water and the organic layer separated. Aqueous HCl was added to aqueous layer to pH 3. This was extracted with ethyl acetate and all of the ethyl acetate extracts were combined. The solution was dried over $MgSO_4$ and the solvent evaporated. Recrystallization from methanol/$H_2O$ provided the compound as white crystals (0.76 g, 92%). Reversed phase HPLC using a gradient system of $CH_3CN/H_2O$ showed a single peak; $^1$H NMR (500 MHz, $CDCl_3$) δ7.38–7.42 (5 H,m), 5.60 (1 H, d), 5.10 (2 H, s), 4.60 (1 H, m), 3.78 (1 H, m), 3.60 (1 H, m), 2.30–1.90 (4 H, m), 1.40 (3 H, d); FABMS 359.1 (M+K), 343.1 (M+Na), 321.1 (M+H); HRFAMBS Calcd for $C_{16}H_{20}N_2O_5K$ (M+K) 359.1006, Found 359.1006; for $C_{16}H_{20}N_2O_5Na$ (M+Na) 343.1270, Found 343.1269; for $C_{16}H_{21}N_2O_5$ (M+H) 321.1450, Found 321.1451.

EXAMPLE 3

N-Benzyloxycarbonly-L-[Alaninyl[9]]didemnin B (9)

Cbz-L-AlaProOH (0.20 g, 0.63 mmol) in 5 mL of $CH_2Cl_2$, NMM (55.9 uL) and DCC (0.13 g, 0.65 mmol) were added at 0° C. to didemnin A (0.47 g, 0.50 mmOl). The solution was allowed to warm to room temperature and stirred for 12 h. Dicyclohexylurea was filtered and washed with ethyl acetate. The filtrate and washings were combined and washed with 10% citric acid, 5% sodium bicarbonate and water, dried over $MgSO_4$ and concentrated. The crude residue was purified by reversed phase HPLC eluting with a gradient system of $CH_3CN/H_2O$ to obtain the product 9, (2.98 g, 69%) as white powder; $^1HNMR$ (500 MHz, CDCl); FABMS 1245.6 (M+H);HRFABMS for $C_{65}H_{97}N_8O_{18}$ (M+H) 1245.7023, Found 1245.7023.

EXAMPLE 4

L-[Alaninyl$^9$] didemnin B (3)

N-Benzyloxycarbonyl-L-[Alaninyl-$^9$] didemnin B (9) (0.10 g, 81.5 umol) was dissolved in isopropyl alcohol (40 mL) and 10% Pd/C catalyst (85.1 mg) was added. The solution was hydrogenated for 3 h, then the catalyst was removed by filtration over celite and solvent was removed to afford 3, which was purified by reversed phase HPLC using a gradient system of acetonitrile/water (82.3 mg, 91%); $^1HNMR$ (500 MHz, CDCl$_3$); FABMS 1111.5 (M+H); HRFABMS Calcd for $C_{57}H_{91}N_8O_{14}$ (M+H) 1111.6655, Found 1111.6664.

EXAMPLE 5

N-Benzyloxycarbonly-L-glutamine (10)

L-Glutamine (1.84 g, 12.62 mmol) was dissolved in 1 N NaOH (12.58 mL) and the solution was cooled to 0° C. and stirred for 30 min, when $Na_2CO_3$ (3.30 g) and benzyl chloroformate (4.38 mL) in dioxane (19.30 mL) were gradually added, in equal portions. Stirring continued at 0° C. for 1 h, then the solution was allowed to stir overnight at room temperature and was extracted with ethyl ether (2×20 mL). The aqueous solution was acidified with 2N HCl to pH 5 and extracted with ethyl acetate (3×50 mL). The ethyl acetate layer was dried over sodium sulfate and evaporated to give an oil, which crystallized overnight. Recrystallization of the crude product gave a white crystalline material (3.07 g, 87%); mp 133–135° C. (Lit. Katsov 133–137° C.); FABMS 319.1 (M+K), 281.1 (M+H); HRFABMS Calcd for $C_{13}H_{17}N_2O_5$: ((M+H) 281.1137, Found 281.1142; Anal. Calcd for $C_{13}H_{17}N_2O_5$ 55.72; H, 5.81; N, 10.01 Found: C, 55.27; H, 5.71; N, 9.83.

EXAMPLE 6

N-Benzyloxycarbonyl-L-glutaminyl-L-[alaninyl$^9$] didemnin B (11)

To a solution of Cbz-L-glutamine (40.0 g, 0.15 mmol) in dry THF (5.0 mL), DMAP (3.22 mg) and DCC (32.0 mg, 0.16 mmol) were added at 20° C. with stirring. Stirring continued at room temperature for 2 h and a solution of L-[Alaninyl$^9$] didemnin B 3, (74.2 mg, 66.3 umol) in DMF (2.50 mL) was added with stirring. The solution was stirred at room temperature for 24 h, diluted with $CH_2C_2$ and washed with 5% $NaHCO_3$ and water to neutral pH. The solution was dried ($Na_2SO_4$) and evaporated to give a white solid which was purified by reversed phase HPLC using a gradient system of acetonitrile/water (56.8 mg, 62%); $^1H$ NMR (500 MHz, CDCl$_3$); FABMS 1373.6 (M+H); HRFABMS Calcd for $C_{70}H_{105}N_{10}O_8$ (M+H) 1373.7608, Found 1373.7608. A second derivative was also obtained from HPLC purification and was found to be bis-[(benzyloxycarbonyl)glutaminyl]-L-[Alaninyl$^9$]-didemnin B (36.0 mg, 20%); FABMS 1635.8 (M+H); HRFABMS Calcd for $C_{83}H_{119}N_{12}O_{22}$ (M+H) 1635.8568, Found 1635.8562.

EXAMPLE 7

L-glutaminyl-L-[alaninyl$^9$]didemnin B (4)

Compound 11 (10.1 mg, 7.30 umol) was dissolved in isopropyl alcohol (2.00 mL) and 10% Pd/C catalyst (10.0 mg) was added. The solution was hydrogenated for 3 h, then the catalyst was removed by filtration over celite and solvent was removed to afford 4 as a white powder (7.92 mg, 89%); $^1H$ NMR (500 MHz, CDCl$_3$); FABMS 1239.7 (M+H); HRFABMS Calcd for $C_{62}H_{99}N_{10}O_{16}$ (M+H) 1239.7241, Found 1239.7245.

EXAMPLE 8

N-Benzyloxycarbonyl-L-pyroglutamic acid

L-Pyroglutamic acid (2.02 g, 13.83 mmol) was dissolved in 1 N NaOH (13.84 mL) and the solution was cooled to 0° C. After 30 min stirring, $Na_2CO_3$ (3.63 g) and benzyl chloroformate (4.82 mL) in dioxane (21.23 mL) were gradually added in equal portions. Stirring was continued at 0° C. for 1 h, then the solution was stirred overnight at room temperature and extracted with ethyl ether (2×20 mL). The aqueous solution was acidified with 2N HCl to pH 5 and extracted with ethyl acetate (3×50 mL). The ethyl acetate layer was dried over sodium sulfate and evaporated to give an oil, which crystallized overnight. Recrystallization of the crude product gave white crystalline material (2.86 g, 87%): FABMS 240.1 (M+H): HRFABMS Calcd for $C_{13}H_{14}NO_5$ (M+H) 264.0872, Found 264.0866; Calcd for $C_{13}H_{13}NaNO_5$ (M+Na) 286.0691, Found 286.0694.

EXAMPLE 9

N-Benzyloxycarbonyl-L-pyroglutamyl-L-glutaminyl-L-[alaninyl$^9$] didemnin B(12)

To a solution of Cbz-pyroglutamic acid (10.2 mg, 38.7 umol) in dry DMF (0.18 mL), DMAP (0.22 mg) and DCC (7.59 mg, 7.74 umol) were added at 20° C. with stirring. Stirring continued at room temperature for 2 h and a solution of L-glutaminyl-L-[alaninyl$^9$] didemnin B (9.60 mg, 7.74 umol) in DMF (2.50 mL) was added with stirring. The solution was stirred at room temperature for 24 h, then diluted with $CH_2Cl_2$ and washed with 5% $NaHCO_3$ and water to neutral pH. The solution was dried ($Na_2SO_4$) and solvent evaporated to give the desired compound as a white solid. The compound was purified by reversed phase HPLC using a gradient system of acetonitrile/water (5.78 mg, 51%); FABMS 1585.8 (M+H); (5.78 mg, 51%); FABMS 1484.8 (M+H); HRFABMS Calcd for $C_{75}H_{110}N_{11}O_{20}$ (M+H) 1484.7929, Found 1484.7932.

EXAMPLE 10

L-pyroglutamyl-L-glutaminyl-L-[alaninyl$^9$] didemnin B (5)

The benzyloxycarbonyl derivative 12 (1.12 mg, 0.70 umol) was dissolved in isopropyl alcohol (1.00 mL) and 10% Pd/C catalyst (1.00 mg) was added. The solution was hydrogenated for 3 h, catalyst was removed by filtration over celite and solvent was removed to afford didemnin M (810 ug, 90%); FABMS 1350.6 (M+H); HRFABMS Calcd for $C_{67}H_{104}N_{11}O_{18}$ (M+H) 1350.7561, Found 1350.7564.

EXAMPLE 11

L-pyroglutamyl-L-[alaninyl$^9$] didemnin B

Pyroglutamic acid (2.50 mg, 22.5 umol) in 0.20 mL of $CH_2Cl_2$, NMM (2.05 uL) and DCC (3.63 mg, 18.3 umol)

were added at 0° C. to didemnin A (8.50 mg, 9.19 umol). The solution was allowed to warm to room temperature and stirred for 12 h. Dicyclohexylurea was filtered and washed with ethyl acetate. The filtrate and washings were combined and washed with 10% citric acid, 5% sodium bicarbonate and water, dried over $MgSO_4$ and concentrated. The crude residue was purified by reversed phase HPLC eluting with a gradient system of $CH_3CN/H_2O$ to obtain the product, (6.40 mg, 59%) as white powder; FABMS 1220.8 (M+H); HRFABMS Calcd for $C_{62}H_{96}N_9O_{16}$ (M+H) 1222.6975, Found 1222.6975.

EXAMPLE 12

N-Benzyloxycarbonyl-L-alaninyl-didemnin A

Cbz-L-alanine (0.20 g, 0.63 mmol) in 5 mL of $CH_2Cl_2$, NMM (55.9 uL) and DCC (0.13 g, 0.65 mmol) were added at 0° C. to didemnin A (0.47 g, 0.50 mmol). The solution was allowed to warm to room temperature and stirred for 12 h. Dicyclohexylurea was filtered and washed with ethyl acetate. The filtrate and washings were combined and washed with 10% citric acid, 5% sodium bicarbonate and water, dried over $MgSO_4$ and concentrated. The crude residue was purified by reversed phase HPLC eluting with a gradient system of $CH_3CN/H_2O$ to obtain the product 11, (2.98 g, 69%) as white powder; $^1$H NMR (500 MHz, $CDCl_3$); FABMS 1148.6 (M+H); HRFABMS Calcd for $C_{60}H_{90}N_7O_{15}$ (M+H) 1148.6495. Found 1148.6495.

EXAMPLE 13

L-Alaninyl-didemnin A (7)

The protected alaninyl didemnin A (1.20 mg, 1.00 umol) was dissolved in isopropyl alcohol (0.50 mL) and 10% Pd/C catalyst (1.00 mg) was added. The solution was hydrogenated for 3 h, then the catalyst was removed by filtration over celite and solvent was removed to afford 7 (0.91 mg, 90%); FABMS 1014.5 (M+H); HRFABMS Calcd for $C_{52}H_{84}N_7O_{13}$ (M+H) 1014.6127, Found 1014.6123.

EXAMPLE 14

N-Benzyloxycarbonyl-L-glutaminyl-didemnin A

Cbz-L-glutamine (10.0 mg, 38.0 umol) in 0.50 ml of $CH_2Cl_2$, NMM (0.55 uL) and DCC (7.60 mg, 38.0 umol) were added at 0° C. to didemnin A (17.9 mg, 19.0 umol). The solution was allowed to warm to room temperature and stirred for 12 h. Dicyclohexylurea was filtered and washed with ethyl acetate. The filtrate and washings were combined and washed with 10% citric acid, 5% sodium bicarbonate and water, dried over $MgSO_4$ and concentrated. The crude residue was purified by reversed phase HPLC eluting with a gradient system of $CH_3CN/H_2O$ to obtain the product, (14.6 mg, 65%) as white powder; FABMS 1205.6 (M+H); HRFABMS Calcd for $C_{62}H_{93}N_8O_{16}$ (M+H) 1205.6710, Found 1205.6716.

EXAMPLE 15

L-Glutaminyl-didemnin A

The protected form of L-Gln-didemnin A (3.20 mg, 2.60 umol) was dissolved in isopropyl alcohol (0.50 mL) and 10% Pd/C catalyst (3.00 mg) was added. The solution was hydrogenated for 3 h, then the catalyst was removed by filtration over celite and solvent was removed to afford L-Gln-DA (2.30 mg, 88%); FABMS 1071.5 (M+H); HRFABMS Calcd for $C_{54}H_{87}N_8O_{14}$ (M+H) 1071.6341, Found 1071.6342.

EXAMPLE 16

N-Benzyloxycarbonyl-L-glutaminyl-L-alaninyl-didemnin A

To a solution of Cbz-L-glutamine (20.0 mg, 75.0 umol) in dry THF (2.0 mL), DMAP (1.61 mg) and DCC (16.0 mg, 80.0 umol) were added at 20° C. with stirring. Stirring continued at room temperature for 2 h and a solution of L-alaninyl-didemnin A 7, (37.1 mg, 33.2 umol) in DMF (2.50 mL) was added with stirring. The solution was stirred at room temperature for 24 h, diluted with $CH_2Cl_2$ and washed with 5% $NaHCO_3$ and water to neutral pH. The solution was dried ($Na_2SO_4$) and evaporated to give a white solid which was purified by reversed phase HPLC using a gradient system of acetonitrile/water (57.3 mg, 60%); $^1$H NMR (500 MHz, $CDCl_3$); FABMS 1276.7 (M+H); HRFABMS Calcd for $C_{65}H_{98}N_9O_{17}$ (M+H) 1276.7081, Found 1276.7086.

EXAMPLE 17

L-glutaminyl-L-alaninyl-didemnin A

The protected form of L-Gln-L-Ala-didemnin A. (1.20 mg, 0.90 umol) was dissolved in isopropyl alcohol (0.05 mL) and 10% Pd/C catalyst (0.80 mg) was added. The solution was hydrogenated for 3 h, then the catalyst was removed by filtration over celite and solvent was removed to afford L-Gln-L-Ala-DA (0.75 mg, 87%); FABMS 1142.7 (M+H); HRFABMS Calcd for $C_{57}H_{92}N_9O_{15}$ (M+H) 1142.6717, Found 1142.6713.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:
1. The compound [$Ala^9$] Didemnin B.
2. The compound Cbz-[$Ala^9$] Didemnin B.
3. The compound Cbz-Ala Didemnin A.
4. The compound Cbz-Gln Didemnin A.
5. The compound $Ala^9$ Didemnin M.
6. The compound Gln-Ala Didemnin A.
7. The compound Cbz-pGlu-Gln-[$Ala^9$]DB.
8. A pharmaceutical or veterinary composition comprising an effective antitumor amount of the substantially pure compound designated herein as [$Ala^9$] Didemnin B and a pharmaceutically acceptable carrier, diluent or excipient.
9. A pharmaceutical or veterinary composition comprising an effective antitumor amount of the substantially pure compound designated herein as Cbz-[$Ala^9$] Didemnin B and a pharmaceutically acceptable carrier, diluent or excipient.
10. A pharmaceutical or veterinary composition comprising an effective antitumor amount of the substantially pure compound designated herein as Cbz-Alaninyl Didemnin A and a pharmaceutically acceptable carrier, diluent or excipient.
11. A pharmaceutical or veterinary composition comprising an effective antitumor amount of the substantially pure compound designated herein as Cbz-Glutaminyl Didemnin A and a pharmaceutically acceptable carrier, diluent or excipient.

12. A pharmaceutical or veterinary composition comprising an effective antitumor amount of the substantially pure compound designated herein as [Ala$^9$] Didemnin M and a pharmaceutically acceptable carrier, diluent or excipient.

13. A pharmaceutical or veterinary composition comprising an effective antitumor amount of the substantially pure compound designated herein as Glutaminyl-Ala Didemnin A and a pharmaceutically acceptable carrier, diluent or excipient.

14. A pharmaceutical or veterinary composition comprising an effective antitumor amount of the substantially pure compound designated herein as Cbz-pGlu-Gln-[Ala$^9$]DB and a pharmaceutically acceptable carrier, diluent or excipient.

15. A method of treating a patient suffering from a mammalian tumor comprising administering to said patient, an effective antitumor amount of the substantially pure compound designated herein as [Ala$^9$] Didemnin B and a pharmaceutically acceptable carrier, diluent or excipient.

16. A method of treating a patient suffering from a mammalian tumor comprising administering to said patient, an effective antitumor amount of the substantially pure compound designated herein as Cbz-[Ala$^9$] Didemnin B and a pharmaceutically acceptable carrier, diluent or excipient.

17. A method of treating a patient suffering from a mammalian tumor comprising administering to said patient, an effective antitumor amount of the substantially pure compound designated herein as Cbz-Alaninyl Didemnin A and a pharmaceutically acceptable carrier, diluent or excipient.

18. A method of treating a patient suffering from a mammalian tumor comprising administering to said patient, an effective antitumor amount of the substantially pure compound designated herein as Cbz-Glutaminyl Didemnin A and a pharmaceutically acceptable carrier, diluent or excipient.

19. A method of treating a patient suffering from a mammalian tumor comprising administering to said patient, an effective antitumor amount of the substantially pure compound designated herein as [Ala$^9$] Didemnin M and a pharmaceutically acceptable carrier, diluent or excipient.

20. A method of treating a patient suffering from a mammalian tumor comprising administering to said patient, an effective antitumor amount of the substantially pure compound designated herein as Glutaminyl-Ala Didemnin A and a pharmaceutically acceptable carrier, diluent or excipient.

21. A method of treating a patient suffering from a mammalian tumor comprising administering to said patient, an effective antitumor amount of the substantially pure compound designated herein as Cbz-pGlu-Gln-[Ala$^9$]DB and a pharmaceutically acceptable carrier, diluent or excipient.

* * * * *

UNITED STATES PATENT AND TRADEMARK OFFICE
CERTIFICATE OF CORRECTION

PATENT NO : 6,034,058
DATED : March 7, 2000
INVENTOR(S) : Kenneth L. Rhinehart, et al.

It is certified that error appears in the above-identified patent and that said Letters Patent are hereby corrected as shown below:

On title page, item 54 Title of the Invention
replace "DILEMNIN"
with --DIDEMNIN--.

Signed and Sealed this

Eighth Day of May, 2001

*Attest:*

NICHOLAS P. GODICI

*Attesting Officer*     Acting Director of the United States Patent and Trademark Office